US009416239B2

(12) United States Patent
Yin et al.

(10) Patent No.: US 9,416,239 B2
(45) Date of Patent: Aug. 16, 2016

(54) ACRYLAMIDE-BASED CROSSLINKING MONOMERS, THEIR PREPARATION, AND USES THEREOF

(71) Applicant: Saltworks Technologies Inc., Vancouver (CA)

(72) Inventors: Xiangchun Yin, Coquitlam (CA); Zhongyuan Zhou, Vancouver (CA); Benjamin Sparrow, Vancouver (CA)

(73) Assignee: SALTWORKS TECHNOLOGIES INC., Vancouver, British Columbia (CA)

( * ) Notice: Subject to any disclaimer, the term of this patent is extended or adjusted under 35 U.S.C. 154(b) by 0 days.

(21) Appl. No.: 14/429,305

(22) PCT Filed: Sep. 27, 2013

(86) PCT No.: PCT/CA2013/000839
§ 371 (c)(1),
(2) Date: Mar. 18, 2015

(87) PCT Pub. No.: WO2014/059516
PCT Pub. Date: Apr. 24, 2014

(65) Prior Publication Data
US 2015/0232627 A1    Aug. 20, 2015

Related U.S. Application Data

(60) Provisional application No. 61/715,993, filed on Oct. 19, 2012.

(51) Int. Cl.
| B01J 47/12 | (2006.01) |
| B01D 61/44 | (2006.01) |
| B01D 67/00 | (2006.01) |
| C08J 5/22 | (2006.01) |
| B01J 39/20 | (2006.01) |
| B01J 41/14 | (2006.01) |

(52) U.S. Cl.
CPC ............... *C08J 5/2243* (2013.01); *B01J 39/20* (2013.01); *B01J 41/14* (2013.01); *C08J 2333/26* (2013.01)

(58) Field of Classification Search
USPC .................................. 427/244; 204/291, 638
See application file for complete search history.

(56) References Cited

U.S. PATENT DOCUMENTS

| 3,274,205 | A | * | 9/1966 | Bikales | ............... | C07D 213/20 |
| | | | | | | 516/15 |
| 3,673,141 | A | * | 6/1972 | Trieschmann et al. | ......... | 524/69 |
| 4,156,065 | A | | 5/1979 | Onder et al. | | |
| 4,231,855 | A | * | 11/1980 | Hodgdon | ............... | B01D 61/46 |
| | | | | | | 204/296 |
| 4,395,531 | A | | 7/1983 | Toyoda et al. | | |
| 4,672,094 | A | | 6/1987 | Nelb et al. | | |
| 5,037,858 | A | | 8/1991 | MacDonald | | |
| 5,118,715 | A | * | 6/1992 | Iglesia et al. | ............... | 518/713 |
| 5,260,483 | A | | 11/1993 | Davis et al. | | |
| 5,527,876 | A | | 6/1996 | Kluth et al. | | |
| 6,232,520 | B1 | | 5/2001 | Hird et al. | | |
| 7,071,353 | B2 | | 7/2006 | Gurtler et al. | | |
| 7,785,751 | B2 | * | 8/2010 | Yamamoto | ............. | C08J 5/2275 |
| | | | | | | 429/493 |
| 8,329,773 | B2 | | 12/2012 | Facke et al. | | |
| 2008/0017578 | A1 | * | 1/2008 | Childs | ............... | B01D 63/06 |
| | | | | | | 210/650 |
| 2008/0020255 | A1 | * | 1/2008 | Hiraoka | ............... | C08J 5/2275 |
| | | | | | | 429/493 |
| 2009/0008328 | A1 | * | 1/2009 | Childs | ............... | B01D 67/0006 |
| | | | | | | 210/635 |
| 2011/0281197 | A1 | * | 11/2011 | Daikoku | ............... | C08F 226/04 |
| | | | | | | 429/480 |
| 2015/0044366 | A1 | * | 2/2015 | Yin | ............... | 427/244 |

FOREIGN PATENT DOCUMENTS

| CA | 1286306 C | 7/1991 |
| DE | 3528098 A1 | 2/1987 |
| JP | 49018849 A | 2/1974 |
| WO | 2004073843 A1 | 9/2004 |
| WO | 2008031595 A2 | 3/2008 |
| WO | 2010106356 A1 | 9/2010 |
| WO | WO-2014/059516 A1 * | 4/2014 |

OTHER PUBLICATIONS

International Search Report and Written Opinion for related PCT Application No. PCT/CA2013/000839 mailed Jan. 13, 2014.
The International Preliminary Report on Patentability for related PCT Application No. PCT/CA2013/000839 mailed Jan. 22, 2015.
Gurtler, et al., "A Catalyst System for the Reaction of Carboxylic Acides with Aliphatic Isocyanates," Tetrahedron Letters, 2004, 45(12), pp. 2515-2521.
Blabrough, et al., "The Condensation Reaction Between Isocyanates and Carboxylic Acids. A Practical Synthesis of Substituted Amides and Anilides," Tetrahedron Letters, 1986, 27(11), pp. 1251-1254.
The first Office Action issued by CIPO against OEE application No. CA 2858238, dated Sep. 15, 2014.
Applicant's Response in CA 2858238 to the first Office Action issued by CIPO, dated Sep. 30, 2014.
The second Office Action issued by CIPO against CA 2858238, dated Oct. 23, 2014.
Applicant's Response in CA 2858238 to the second Office Action issued by CIPO, dated Dec. 1, 2014.
The Notice of Allowance for CA 2858238 issued by CIPO, dated Jan. 8, 2015.
European Search Report issued in related European Patent Application No. 13846684.2 mailed May 1, 2016.

* cited by examiner

*Primary Examiner* — Peter D Mulcahy
*Assistant Examiner* — Henry Hu
(74) *Attorney, Agent, or Firm* — Troutman Sanders LLP; Ryan A. Schneider; Chris N. Davis

(57) ABSTRACT

A process for preparing an acrylamide-based crosslinking monomer comprising reacting in the presence of a catalyst an isocyanate compound containing at least two isocyanate groups with one of acrylic acid or methacrylic acid. These acrylamide-based crosslinking monomers are used in the preparation of coating compositions, adhesive compositions curable by applying thermal or radiation energy, and in the preparation of cation or anion exchange membranes.

4 Claims, No Drawings

ACRYLAMIDE-BASED CROSSLINKING MONOMERS, THEIR PREPARATION, AND USES THEREOF

CROSS-REFERENCE TO RELATED APPLICATIONS

This application is a US National Stage of International Application No. PCT/CA2013/000839, filed 27 Sep. 2013, which claims the benefit of US Provisional Patent Application No. 61/715,993, filed 19 Oct. 2012, each herein fully incorporated by reference.

TECHNICAL FIELD

This disclosure relates to acrylamide-based crosslinking monomers and methacrylamide-based crosslinking monomers. More particularly, this disclosure relates to processes for preparing acrylamide-based crosslinking monomers and methacrylamide-based crosslinking monomers, and to their uses for preparing adhesives, membranes, coatings, and ion exchange resin.

BACKGROUND

Free-radical crosslinking polymerizations and copolymerizations of crosslinking monomers with two or more ethylenic groups have been used for preparation of coatings, adhesives, membrane formations and resin preparations. These crosslinking monomers are generally multifunctional acrylate monomers and methacrylate monomers exemplified by hexanediol diacrylate, or alternatively, are acrylated oligomers exemplified by acrylated urethanes, epoxies, polyesters and acrylics. They are commercially available from coating chemical suppliers exemplified by Sartomer USA LLC (Exton, Pa., USA) and Cytec Industries Inc. (Woodland Park, N.J., USA). A disadvantage of these acrylic/methacrylic ester crosslinking monomers is that they degrade rapidly in the presence of caustic substance such as sodium hydroxide solution or in the presence of acid substance such as hydrochloric acid.

In contrast, acrylamide-based crosslinking monomers are much stable under caustic/acidic conditions. N,N'-methylenebisacrylamide only shows slight degradation at pH 14. Methylenebisacrylamide is a crystalline compound and its crosslinking network is very brittle. In addition, methylenebisacrylamide has low solubility (less than 10 wt %) in general solvents such as ethanol, water, and N-methyl pyrrolidone and thus has limited uses in coatings and resins where relatively high crosslinking density is required. Typical processes for preparation of acrylamide-based monomers generally comprise reacting an amine compound with one of an anhydride and an acid chloride. Such processes use expensive and hazardous acid chlorides or anhydride and generate byproducts that are difficult and expensive to remove. There are no other acrylamide-based crosslinking monomers commercially available.

SUMMARY

The embodiments of the present disclosure pertain to processes for preparation of acrylamide-based crosslinking monomers comprising reacting in the presence of a catalyst, an isocyanate compound having at least two isocyanate groups with acrylic acid. Some aspects relate to processes for preparation of methacrylamide-based crosslinking monomers comprising reacting in the presence of a catalyst, an isocyanate compound having at least two isocyanate groups with methacrylic acid. Suitable isocyanate compounds for use in the processes disclosed herein are exemplified by aliphatic isocyanates, cycloaliphatic isocyanates, aromatic isocyanates and oligomer isocyanates containing at least two isocyanate groups.

Some embodiments of the present disclosure pertain to use of the acrylamide-based crosslinking monomers and/or the methacrylamide-based crosslinking monomers in processes for preparation of coatings for applications to substrates exemplified by metals, plastics, woody materials, and paper goods.

Some embodiments of the present disclosure pertain to use of the acrylamide-based crosslinking monomers and/or the methacrylamide-based crosslinking monomers in processes for preparation of adhesives for use in applications where good hydrolytical stability is desired.

Some embodiments of the present disclosure pertain to use of the acrylamide-based crosslinking monomers and/or the methacrylamide-based crosslinking monomers in processes for preparation of ion exchange membranes where good hydrolytical stability is desired.

Some embodiments of the present disclosure pertain to use of the acrylamide-based crosslinking monomers and/or the methacrylamide-based crosslinking monomers in processes for preparation of ion exchange resins. Some aspects pertain to processes for preparation of cation exchange resins, and to cation exchange resins comprising one of the acrylamide-based crosslinking monomers or the methacrylamide-based crosslinking monomers prepared by the processes disclosed herein. Some aspects pertain to processes for preparation of anion exchange resins, and to anion exchange resins comprising one of the acrylamide-based crosslinking monomers or the methacrylamide-based crosslinking monomers prepared by the processes disclosed herein.

DETAILED DESCRIPTION

The embodiments of the present disclosure pertain to processes for producing acrylamide-based crosslinking monomers and methacrylamide-based crosslinking monomers comprising reacting in the presence of a catalyst an isocyanate compound containing at least two isocyanate groups with one of acrylic acid and methacrylic acid (Scheme 1). The acrylamide-based crosslinking monomers and methacrylamide-based crosslinking monomers are synthesized from readily available isocyanates as starting materials. The acrylamide-based crosslinking monomers and methacrylamide-based crosslinking monomers are suitable for use in applications where good hydrolytical stability is required, for example in coatings, adhesives, membrane preparations, and resin preparations among others.

Scheme 1:

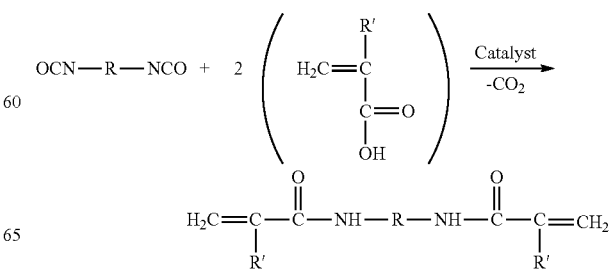

wherein R is one of an aliphatic group, a cycloaliphatic group, an aromatic group, an aliphatic polyisocyanate group, a polyether oligomer group, a polyurethane oligomer group, or a polyurea oligomer group. R' is a hydrogen atom or a methyl group.

Suitable aliphatic isocyanates or cycloaliphatic isocyanates are exemplified by butane diisocyanate, cyclohexane diisocyanate, dicyclohexylmethane 4,4'-diisocyanate (HMDI), hexamethylene diisocyanate (HDI), isophorone diisocyanate (IPDI), 2,2,4-trimethylhexamethylene diisocyanate, tetramethylxylene diisocyanate (TMXDI), and xylene diisocyanate, among others.

Suitable aromatic isocyanates are exemplified by dianisidine diisocyanate, 3,3'-dimethylphenyl-4,4'-diisocyanate, methylene diphenyl diisocyanate (MDI), 1,5-naphthalene diisocyanate, phenylene diisocynate (PDI), triphenylmethane-4,4',4"-triisocyanate, and toluene diisocyanate (TDI), among others.

Suitable oligomer isocyanates are exemplified by DESMODUR® polyisocyanates such as DESMODUR® N 100, DESMODUR® N 3300A, and DESMODUR® N 3400 (DESMODUR is a registered trademark of Bayer Aktiengesellschaft, Leverkusen, Fed. Rep. Germany), ISONATE® prepolymers exemplified by ISONATE® 181 and ISONATE® M340 (ISONATE is a registered trademark of the Dow Chemical Company, Midland, Mich., USA), VESTANAT® polyisocyanates such as VESTANAT® 2500 and VESTANAT® 2640 (VESTANAT is a registered trademark of Evonik Deguss GMBH, Essen, Fed. Rep. Germany), and by poly(propylene glycol) tolylene 2,4-diisocyanate (Sigma-Aldrich Canada Co., Oakville, ON, Canada). Such exemplary isocyanates may be used alone, or alternatively, in combinations of two or more.

Suitable carboxylic acids monomers are exemplified by acrylic acid and methacrylic acid, among others.

The amount of the isocyanate compound and the amount of acrylic acid or alternatively, methacrylic acid preferably allows acrylic acid or methacrylic acid to be used up. Typically, the molar ratio of the isocyanate group to the carboxylic acid group is about 1.0 to about 2.0. At the end of the reaction, excess isocyanate groups could be capped by reacting with amine compounds such as butylamine or 1,5-pentanediamine, hydroxyl compounds such as 1,6-hexanediol or water. In some cases, additional functional groups or extended linkage length between acrylamido-groups could be introduced into the acrylamide-based crosslinking monomers from the capping compounds. In some cases, the excess isocyanate groups could be used as functionalities of the final products for applications such as adhesives that chemically bond to the substrate surface via isocyanate reactions.

Suitable catalysts are exemplified by organometallic compounds, metal salts, and tertiary amines, among others. These catalysts may be used alone or in combinations of two or more.

Suitable organometallic catalysts are exemplified by aluminium acetylacetonate, dibutyltin dichloride, dibutyltin dilaurate, and magnesium acetylacetonate, among others.

Suitable metal salt catalysts are based on elements of Groups IIA, IIIA, IB and IIB of the periodic table. Particularly useful salts are exemplified by aluminum triethoxide, aluminum chloride, bismuth(III) acetate, bismuth(III) 2-ethylhexanoate, bismuth(III) neodecanoate, calcium chloride, calcium perchlorate, calcium stearate, magnesium n-propoxide, magnesium chloride, magnesium 2,4-pentanedionate, magnesium trifluoro-methylsulfonate, magnesium perchlorate, magnesium stearate, scandium(III) trifluoromethanesulfonate, scandium(III) acetate, zinc 2-ethylhexanoate, and zinc acetate, among others. Particularly suitable catalysts are aluminum chloride, calcium chloride, magnesium chloride, and zinc acetate, among others.

Suitable tertiary amine catalysts are exemplified by 1,4-diazabicyclo-(2,2,2)-octane, 1-methyl imidazole, triethyl amine, and N-methyl-N'-dimethylaminoethyl piperazine, among others.

The amount of catalysts useful in the present disclosure depends on the reactivity of isocyanate compounds. Any amount of catalyst may be used up to the solubility limit of the catalyst in the reaction solution. However, particularly suitable amounts of catalyst are in the range of about 0.001 wt % to about 10 wt % of the total solution weight.

Suitable solvents are exemplified by chloroform, dichloromethane, dimethylacetamide, ethylene glycol dimethyl ether, N-methylpyrrolidone, and tetrahydrofuran, among others. In one embodiment, the product of synthesized acrylamide-based crosslinking monomer may precipitate out of the solution during reaction, and a pure and solid product can be obtained by filtration after the reaction has occurred. In another embodiment, the synthesized acrylamide-based crosslinking monomer is prepared in a solvent to form a 10 wt % to a 90 wt % solution, preferably a 30 wt % to a 80 wt % solution. After the reaction has been carried out, the solvent could be removed from the reaction product or alternatively, be kept as a diluent in the product solution for further applications.

The processes of the present disclosure may be carried out at a wide range of temperatures. High reaction temperature helps the elimination of carbon dioxide byproduct and drives the reaction to a high conversion. However, excessively high temperature leads to self-polymerizations of acrylic acid monomer and the product of acrylamide-based crosslinking monomers. Suitable reaction temperatures are in the range of about 15° C. to about 80° C. Particularly suitable reaction temperatures are in the range of about 30° C. to about 70° C.

Exemplary uses of the acrylamide-based crosslinking monomers and the methacrylamide-based crosslinking monomers disclosed herein include among others, radical crosslinking polymerizations and copolymerizations for preparation of coatings, adhesives, membranes, resins, and other preparations where good hydrolytical stability is required.

One embodiment pertains to use of the acrylamide-based crosslinking monomers and the methacrylamide-based crosslinking monomers produced as disclosed herein, in coating compositions for primers and/or topcoats for applications onto wood, paper, plastic, aluminum, steel, galvanized metals, and other types of metals. The acrylamide-based crosslinking monomers and the methacrylamide-based crosslinking monomers can be used alone or alternatively, in combination with other monomers and/or polymers to impart desirable characteristics to the compositions, exemplified by flexibility, adhesion, crosslinking, flowability and leveling during application. The resulting compositions may be applied to target surfaces by spraying, rolling, dipping, curtain coating, and other conventional processes. Curing of such coatings is achieved by free-radical crosslinking polymerizations initiated through thermal initiation or radiation initiation. Suitable radiation initiation is exemplified by UV beams and electron beams. It is preferable to incorporate into the coating compositions one or more photoinitiators that release free radicals upon exposure to UV light. Suitable photoinitiators are exemplified by α-hydroxy ketones, benzoin ethers, benzil ketals, α-dialkoxy acetophenones, α-hydroxy alkylphenones, α-amino alkylphenones, acylphophine oxides, benzophenons/amines, thioxanthone/amines, and titanocenes. Suitable α-hydroxy ketone free radical initiators are exemplified by 2-hydroxy-1-[4-(2-hydroxyethoxyl)phenyl]-2-methyl-1-propanone, 2-hydroxy-2-methyl-1-phenyl-1-propanone, 1-hydroxy-cyclohexyl-phenyl-ketone, 1-hydroxy-cyclohexyl-phenyl-ketone:benzophenone, and mixtures thereof.

Another embodiment pertains to use of the acrylamide-based crosslinking monomers and the methacrylamide-based crosslinking monomers produced as disclosed herein, for preparation of radiation-curable adhesive compositions. Such compositions may be curable, for example, with UV beams or with electron beams. The radiation-curable adhesive compositions preferably comprise about 0.01 wt % to 10 wt % of selected photoinitiators. In some cases, additional free isocyanate functionality in the acrylamide-based crosslinking monomers and the methacrylamide-based crosslinking monomers can be added for promotion of covalent bonding between substrates and the adhesive compositions. The amount of free isocyanate functionality can be controlled during the synthesis of the acrylamide-based crosslinking monomers and the methacrylamide-based crosslinking monomers by the addition of extra equivalents of isocyanate functionality to acrylic acid functionality or alternatively to methacrylic acid functionality, for example in the range of about 1.1:1 to about 1.5:1.

Another embodiment pertains to the use of the acrylamide-based crosslinking monomers and the methacrylamide-based crosslinking monomers produced as disclosed herein for preparation of films and membranes having good mechanical properties and hydrolytical stability. Membrane hydrolysis is a critical issue in most water treatment processes. Ion exchange membranes produced from acrylamide-based crosslinking monomers and the methacrylamide-based crosslinking monomers show good hydrolytical stability under caustic/acidic conditions. Suitable ion exchange membranes can be prepared from a monomer mixture of ionic monomers and crosslinking monomers, wherein the monomer mixture contains 10 wt % to 60 wt % of crosslinking monomers based on the total monomer weight. Exemplary ionic monomers that can be mixed with the acrylamide-based crosslinking monomers disclosed herein include: (i) monomers having a negatively charged ionic group for preparation of cation exchange membranes, and (ii) monomers having a positively charged ionic group for preparation of anion exchange membranes. Suitable negatively charged ionic monomers for preparing cation exchange membranes are exemplified by (meth)acrylic acid, carboxyethyl acrylate, sodium 4-vinylbenzenesulfonate, 3-sulfopropyl acrylate potassium salt, 2-acrylamido-2-methyl-1-propanesulfonic acid, and vinylsulfonic acid. Suitable positively charged ionic monomers for preparing anion exchange membranes are exemplified by 3-acrylamidopropyl trimethylammonium chloride, 2-acryloyloxyethyl trimethylammonium chloride, 2-methacryloyloxyethyl trimethylammonium chloride, 3-methacryloylaminopropyl trimethylammonium chloride, and vinylbenzyl trimethylammonium chloride.

Another embodiment pertains to the use of the acrylamide-based crosslinking monomers and the methacrylamide-based crosslinking monomers produced as disclosed herein for preparation of ion exchange resins having good mechanical properties and hydrolytical stability. The rigidity and mechanical strength of ion exchange resins tend to increase with the amount of crosslinking monomers in the monomer mixture. When lower levels of the crosslinking monomers are used, ion exchange resins tend to form gels, while higher levels of the crosslinking monomers tend to form spherical resins. The high solubility of acrylamide-based crosslinking monomers in a general solvent is advantageous. For example, ion exchange resins can be prepared from a mixture of ionic monomers and acrylamide-based crosslinking monomers disclosed herein or alternatively the methacrylamide-based crosslinking monomers, wherein the mixture contains about 10 wt % to about 90 wt % of crosslinking monomers based on the total monomer weight. Exemplary ionic monomers suitable for mixing with the present acrylamide-based crosslinking monomers and the methacrylamide-based crosslinking monomers include: (i) monomers having a negatively charged ionic group for preparation of cation exchange resin, and (ii) monomers having a positively charged ionic group for preparation of anion exchange resins. Suitable negatively charged ionic monomers for preparing a cation exchange resin include, but are not limited to, (meth)acrylic acid, carboxyethyl acrylate, sodium 4-vinylbenzenesulfonate, 3-sulfopropyl acrylate potassium salt, 2-acrylamido-2-methyl-1-propanesulfonic acid, and vinylsulfonic acid. Suitable positively charged ionic monomers for preparing an anion exchange resin include, but are not limited to, 3-acrylamidopropyl trimethylammonium chloride, 2-acryloyloxyethyl trimethylammonium chloride, 2-methacryloyloxyethyl trimethylammonium chloride, 3-methacryloylaminopropyl trimethylammonium chloride, and vinylbenzyl trimethylammonium chloride.

The present disclosure will be further illustrated in the following examples. However it is to be understood that these examples are for illustrative purposes only, and should not be used to limit the scope of the present disclosure in any manner.

EXAMPLES

Example 1

Synthesis of Methacrylamide-Based Crosslinking Monomer 4,4'-Methylene Bis(Phenyl Methacrylamide)

A 250-ml three-neck flask equipped with a stirrer, a thermometer, and a condenser, was charged with methacrylic acid (4.8 g), 4-methoxyphenol (0.02 g), and aluminium chloride (0.37 g). The mixture was stirred at ambient room temperature (i.e., in a range of about 15° C. to about 30° C.) to form a solution which was then heated to 40° C. in an oil bath. To this solution was gradually added 45 wt % methylene diphenyl diisocyanate (MDI) in dimethylacetamide solution (15.6 g) within a 1-h time period. The reaction mixture was maintained at about 40° C. for 3 h until a barely noticeable evolution of $CO_2$ bubbles was evident, to produce the crosslinking monomer 4,4'-methylene bis(phenyl methacrylamide) in dimethylacetamide solution. The final product was titrated with dibutyl amine to detect and quantify its isocyanate content, and was determined to be isocyanate-free.

Example 2

Synthesis of Acrylamide-Based Crosslinking Monomer 1,6-Hexamethylene Diacrylamide A 250-ml three-neck flask equipped with a stirrer, a thermometer, and a condenser was charged with acrylic acid (7.2 g), 4-methoxyphenol (0.02 g), N-methyl pyrrolidone (20.0 g), and magnesium chloride (0.047 g). The mixture was stirred at room temperature to form a solution. To this solution was gradually added within a 1-h period, 8.4 g of hexamethylene diisocyanate (HDI). Generation of $CO_2$ gas began immediately and the product started to precipitate from the solution within 10 min after addition of the HDI. The reaction mixture was heated for 2 h at 40° C. after the addition of HDI. The precipitate product was filtered, washed with diethyl ether, and dried under vacuum at room temperature.

Example 3

Synthesis of Acrylamide-Based Crosslinking Monomer 4,4'-Methylene Bis(Phenyl Acrylamide)

A 250-ml three-neck flask equipped with a stirrer, thermometer, and condenser was charged with acrylic acid (4.7 g), 4-methoxyphenol (0.02 g), and 1-methyl imidazole (0.82 g). The mixture was stirred at room temperature to form a solution. To this solution was gradually added within a 1-h period, 45 wt % methylene diphenyl diisocyanate (MDI) in dimethylacetamide solution (18.0 g) to keep the exotherm temperature below 40° C. Generation of $CO_2$ gas began immediately upon addition of MDI and became more rapid after 10 min. The solution became viscous and was stirred overnight at room temperature until barely noticeable evolution of $CO_2$ bubbles, to obtain the crosslinking monomer 4,4'-methylene bis(phenyl acrylamide) in dimethylacetamide solution.

Example 4

Synthesis of Acrylamide-Based Crosslinking Monomer Trimethyl Hexamethylene Diacrylamide A 250-ml three-neck flask equipped with a stirrer, thermometer, and condenser was charged with acrylic acid (7.2 g), 4-methoxyphenol (0.023 g), butylated hydroxytoluene (0.023 g), tetrahydrofuran (13.3 g) and magnesium chloride (0.047 g). The mixture was stirred at room temperature to form a solution and then was heated to 60° C. in an oil bath. To this solution was gradually added within a 1-h period, 10.5 g of trimethyl hexamethylene diisocyanate. The reaction mixture was kept at 60° C. for 3.5 h until the evolution of $CO_2$ bubbles had substantially ceased. The solution was cooled after which the solvent tetrahydrofuran was removed by rotary evaporation followed by vacuum at room temperature. The final product was a clear and viscous liquid at room temperature, and its structure was confirmed by $^1$H-NMR.

Example 5

Synthesis of Acrylamide-Based Crosslinking Monomer Trimethyl Hexamethylene Diacrylamide A 250-ml three-neck flask equipped with a stirrer, thermometer, and condenser was charged with acrylic acid (7.2 g), 4-methoxyphenol (0.034 g), N-methyl pyrrolidone (3.3 g) and magnesium chloride (0.047 g). The mixture was stirred at room temperature to form a solution and then was heated to 70° C. in an oil bath. To this solution was gradually added within a 1-h period, 10.5 g of trimethyl hexamethylene diisocyanate. The reaction mixture was kept at 70° C. for 3 h until the evolution of $CO_2$ bubbles had substantially ceased. The solution was cooled down to room temperature to obtain trimethylhexamethylene diacrylamide in N-methyl pyrrolidone solution.

Example 6

Synthesis of Acrylamide-Based Crosslinking Monomer Trimethyl Hexamethylene Diacrylamide A 250-ml three-neck flask equipped with a stirrer, thermometer, and condenser was charged with acrylic acid (7.2 g), 4-methoxyphenol (0.023 g), butylated hydroxytoluene (0.023 g), tetrahydrofuran (13.3 g) and magnesium chloride (0.047 g). The mixture was stirred at room temperature to form a solution and then was heated to 60° C. in an oil bath. To this solution was gradually added within a 1-h period, 11.6 g of trimethyl hexamethylene diisocyanate. The reaction mixture was kept at 60° C. for 3.5 h until barely noticeable evolution of $CO_2$ bubbles. The solution was cooled after which the solvent tetrahydrofuran was removed by rotary evaporation followed by vacuum at room temperature. The viscous and clear liquid product was stored for adhesive application.

Example 7

Synthesis of Acrylamide-Based Crosslinking Monomer 4,4'-Methylene Bis(Cyclohexyl Acrylamide)

A 250-ml three-neck flask equipped with a stirrer, thermometer, and condenser was charged with acrylic acid (5.0 g), 4-methoxyphenol (0.022 g), N-methyl pyrrolidone (4.8 g) and magnesium chloride (0.033 g). The mixture was stirred at room temperature to form a solution and was then heated to 70° C. in an oil bath. To this solution was gradually added within a 1-h period, 9.2 g of dicyclohexylmethane 4,4'-diisocyanate (HMDI). The reaction mixture was kept at 70° C. for 3 h until the evolution of $CO_2$ bubbles had substantially ceased indicating that the formation of 4,4'-methylene bis(cyclohexyl acrylamide) in N-methyl pyrrolidone solution was completed.

Example 8

Synthesis of Acrylamide-Based Crosslinking Monomer Isophorone Diacrylamide

A 250-ml three-neck flask equipped with a stirrer, thermometer, and condenser was charged with acrylic acid (7.2 g), 4-methoxyphenol (0.046 g), N-methyl pyrrolidone (6.0 g), magnesium chloride (0.047 g). The mixture was stirred at room temperature to form a solution and was then heated to 70° C. in an oil bath. To this solution was gradually added within a 1-h period, 11.1 g of isophorone diisocyanate (IPDI). The reaction mixture was kept at 70° C. for 3 h until the evolution of $CO_2$ bubbles had substantially ceased. The solution was cooled down to room temperature to obtain isophorone diacrylamide in N-methyl pyrrolidone solution.

Example 9

Synthesis of Acrylamide-Capped Oligomer Crosslinking Monomer

A solution of 10 g of DESMODUR® N 100 (aliphatic polyisocyanate oligomer) mixed with 12 g of N-methyl pyrrolidone in a glass vessel at 70° C. Magnesium chloride (0.01 g) was dissolved in acrylic acid (3.8 g) and then added into the DESMODUR® N 100 solution under constant stirring at 70° C. The reaction mixture was kept at 70° C. for 3 h until the evolution of $CO_2$ bubbles had substantially ceased, indicating that development of acrylamide-capped oligomer in N-methyl pyrrolidone solution had occurred.

Example 10

Synthesis of Acrylamide-Based Crosslinking Monomer Having Urethane Group in the Linking Between Acrylamido-Groups A 250-ml three-neck flask equipped with a stirrer, thermometer, and condenser was charged with acrylic acid (7.2 g), 4-methoxyphenol (0.046 g), N-methyl pyrrolidone (7.7 g), magnesium chloride (0.047 g), and dibutyltin dilaurate (0.23 g). The mixture was stirred at room temperature to form a solution and was then heated to 70° C. in an oil bath. To this solution was gradually added within a 1-h period, 22.2 g of isophorone diisocyanate (IPDI). The reaction mixture was kept at 70° C. for 3 h until the evolution of $CO_2$ bubbles had substantially ceased. The solution was cooled down to room temperature. After 5.9 g of 1,6-hexanediol was added, the solution was stirred for another 10 h to obtain a solution of acrylamide-based crosslinking monomer having a urethane group in the linking between acrylamido-groups Example 11

Synthesis of Acrylamide-Based Crosslinking Monomer Having Urea Group in the Linking Between Acrylamido-Groups A 250-ml three-neck flask equipped with a stirrer, thermometer, and condenser was charged with acrylic acid (7.2 g), 4-methoxyphenol (0.046 g), N-methyl pyrrolidone (20.0 g), and magnesium chloride (0.047 g). The mixture was stirred at room temperature to form a solution and was then heated to 70° C. in an oil bath. To this solution was gradually added within a 1-h period, 22.2 g of isophorone diisocyanate (IPDI). The reaction mixture was kept at 70° C. for 3 h until the evolution of $CO_2$ bubbles had substantially ceased. The solution was cooled down to room temperature. After addition of 5.1 g of 1,5-pentanediamine, the solution was stirred for another 1 h to obtain a solution of acrylamide-based crosslinking monomer having urea group in the linking between acrylamido-groups.

Example 12

Synthesis of Acrylamide-Based Crosslinking Monomer Having Extended Linking Length Between Acrylamido-Groups A 250-ml three-neck flask equipped with thermometer and condenser was charged with acrylic acid (0.36 g), 4-methoxyphenol (0.003 g), N-methyl pyrrolidone (2.0 g), and magnesium chloride (0.01 g). The mixture was stirred with a magnetic stirrer at room temperature to form a solution and was then heated to 70° C. in an oil bath. To this solution was gradually added within a 1-h period, 1.1 g of isophorone diisocyanate (IPDI). The reaction mixture was kept at 70° C. for 1 h until the evolution of $CO_2$ bubbles had substantially ceased. The solution was cooled down to room temperature. After addition of poly(ethylene glycol) diamine (Mn 2000, 5.0 g), the solution was stirred for another 1 h to obtain a solution of acrylamide-based crosslinking monomer having polyethylene glycol as a linkage between acrylamido-groups.

Example 13

Coating Composition with Trimethylhexamethylene Diacrylamide Crosslinking Monomer A UV-curable coating formula was prepared by mixing 5.0 g of trimethylhexamethylene diacrylamide crosslinking monomer from Example 4 and 0.1 g of the photoinitiator IRGACURE® 2959 (IRGACURE is a registered trademark of CIBA Specialty Chemicals Corp., Tarrytown, N.Y., USA). The mixture was coated on the surfaces on a flat glass plate by running a doctor blade with coating thickness of about 200 µm. The coating was then irradiated with UV light (wavelength 300-400 nm) for 5 min. The hardness of the coating was tested by rubbing the coating back-and-forth with an acetone-wicked gauze and no obvious scratch was found. The solid content of the coating was tested by dipping the coating in tetrahydrofuran solvent at room temperature for 24 h and the weight different of the coating before and after dipping was less than 4%.

Example 14

Adhesive Composition with Trimethylhexamethylene Diacrylamide Crosslinking Monomer A UV curable adhesive formula was prepared by mixing 5.0 g of trimethylhexamethylene diacrylamide crosslinking monomer from Example 6 and 0.1 g of IRGACURE® 2959. The adhesive composition was applied onto a microscope glass slide (25×75×1 mm) in a thin layer having a thickness of about 1 µm to about 5 µm. Another microscope glass slide was carefully laid on top of the adhesive coating. The slide sandwich assembly was then irradiated with UV light (wavelength 300-400 nm) for 5 min. The strength of the adhesion was tested by taping two pieces of gorilla tapes (Gorilla glue company) onto the outside surfaces of the glass slide assembly and rapidly pulling the tapes away from the assembly. The glass slide assembly was not separated by the tape pulling.

Example 15

Film Formation with 4,4'-Methylene Bis(Phenyl Methacrylamide) Crosslinking Monomer A coating formula was prepared by mixing 5.0 g of the reaction product from Example 1 with 0.15 g of IRGACURE® 2959. The solution was spread onto a 90-µm thick non-woven polypropylene fabric sheet with 80% porosity (DelStar Technologies Inc., Middleton, Del., USA) between two polyethylene sheets. The polyethylene sandwich assembly was irradiated with UV light (wavelength 300-400 nm) for 10 min to cure the coating. The sandwich was separated and the film was placed into water to leach out the solvent. The resulting film was yellowish, hard and tough.

Example 16

Film Formation with Acrylamide-Capped Oligomer Crosslinking Monomer

A coating formula was prepared by mixing 5 g of the reaction product from Example 9 with 0.15 g of IRGACURE® 2959. The solution was spread onto a 90-µm thick non-woven polypropylene substrate sheet with 80% porosity (DelStar Technologies Inc., Middleton, Del., USA) between two polyethylene sheets. The polyethylene sandwich assembly was then irradiated with UV light (wavelength 300-400 nm) for 10 min to cure the coating. The sandwich was separated and the film was placed into water to leach out the solvent. The resulting film was clear, hard and flexible (e.g., the film could be bent 180° without cracking, ripping or tearing).

Example 17

Preparation of Cation Exchange Membrane (CEM) with Crosslinking Monomer 4,4'-Methylene Bis(Cyclohexyl Acrylamide)

2-acrylamido-2-methyl-1-propanesulfonic acid (AMPS) (10.0 g) was dissolved in 10.0 g of dimethylacetamide (DMAc). To this solution was added 14.3 g of the 4,4'-methylene bis(cyclohexyl acrylamide) crosslinker solution from Example 7 and the solution was further mixed. IRGACURE® 2959 (2.5 g) was then added to and dissolved in the mixture. The solution was applied onto SEFAR® PET 1500 woven polyester cloth (mesh open 151 μm, open area 53%, and mesh thickness 90 μm) (SEFAR is a registered trademark of Sefar Holding AG Corp., Thal, Switzerland). Excess solution was removed from the substrate by running a roller over the substrate with care being taken to exclude air bubbles from the substrate. The solution-impregnated substrate was irradiated with UV light (wavelength 300-400 nm) for 10 min. The resulting cation exchange membrane was rinsed thoroughly in water and was then placed in 10 wt % NaCl solution to convert the membrane into sodium form. The cation exchange membrane had the following properties:
  Membrane thickness: 0.09 mm-0.10 mm
  Electrical resistance: 1.0-1.4 Ωcm2
  Water content: 42.5 wt %
  Ion exchange capacity: 2.4 mmol per gram of dry resin Example 18

Preparation of Anion Exchange Membrane (AEM) with Crosslinking Monomer 4,4'-Methylene Bis(Cyclohexyl Acrylamide)

3-methacryloylaminopropyl trimethylammonium chloride (MAPTAC) (10.0 g) was dissolved in 6.5 g of 1.3-butanediol/water (90/10 wt/wt). To this solution was added 14.3 g of the 4,4'-methylene bis(cyclohexyl acrylamide) crosslinker solution from Example 7, and further mixed. IRGACURE® 2959 (2.5 g) was then added to and dissolved in the mixture. The resulting solution was applied onto SEFAR® PET 1500 woven polyester cloth (mesh open 151 μm, open area 53%, and mesh thickness 90 μm). Excess solution was removed from the substrate by running a roller over the substrate with care being taken to exclude air bubbles from the substrate. The solution-impregnated substrate was irradiated with UV light (wavelength 300-400 nm) for 10 min. The resulting anion exchange membrane was rinsed thoroughly in water. The anion exchange membrane had the following properties:
  Membrane thickness: 0.09 mm-0.10 mm
  Electrical resistance: 1.5-2.0 Ωcm2
  Water content: 35.0 wt %
  Ion exchange capacity: 2.2 mmol per gram of dry resin Example 19

Hydrolytical Stability of Ion Exchange Membranes

The caustic stabilities of the cation exchange membrane (CEM) from Example 17 and of the anion exchange membrane (AEM) from Example 18 were tested by soaking the membranes in 0.1 M sodium carbonate/3.0 M sodium chloride solution with pH 10.8 at 60° C. Membrane performances are summarized in Table 1. The permselectivity of the membranes were measured in solutions of 0.6 M sodium chloride solution vs. 0.02 M sodium chloride solution.

TABLE 1

Performance of the membrane under caustic solution (pH 10.8) at 60° C.

| | Cation exchange membrane | | | Anion exchange membrane | | |
|---|---|---|---|---|---|---|
| Time | Resistance | Permselectivity | Water content | Resistance | Permselectivity | Water content |
| 0 | 1.2 Ωcm$^2$ | 92.0% | 42.5% | 1.5 Ωcm$^2$ | 88.0% | 35.0% |
| 1 month | 1.2 Ωcm$^2$ | 92.0% | 40.4% | 1.5 Ωcm$^2$ | 88.0% | 35.7% |
| 2 months | 1.2 Ωcm$^2$ | 92.0% | 43.0% | 1.5 Ωcm$^2$ | 88.0% | 33.8% |

Example 20

Preparation of Cation Exchange Membrane (CEM) with Crosslinking Monomer Trimethyl Hexamethylene Diacrylamide 2-acrylamido-2-methyl-1-propanesulfonic acid (AMPS) (10.0 g) was first dissolved in dimethylacetamide (DMAc) (10.0 g). To this solution was added and thoroughly mixed 12.5 g of trimethyl hexamethylene diacrylamide crosslinker solution from Example 5 after which IRGACURE® 2959 (0.8 g) was added and dissolved in the formula solution. The formula solution was applied onto SEFAR® PET 1500 woven polyester cloth (mesh open 151 μm, open area 53%, and mesh thickness 90 μm). Excess solution was removed from the substrate by running a roller over the substrate with care taken to exclude air bubbles from the substrate. The solution-impregnated substrate was irradiated with UV light (wavelength 300-400 nm) for 10 min. The resulting cation exchange membrane was rinsed thoroughly in water and was then placed in 10 wt % NaCl solution to convert the membrane into sodium form. The cation exchange membrane had the following properties:
  Membrane thickness: 0.09 mm-0.10 mm
  Electrical resistance: 1.2-1.5 Ωcm2
  Water content: 37.0 wt %
  Ion exchange capacity: 2.4 mmol per gram of dry resin Example 21

Preparation of Anion Exchange Membrane (AEM) with Crosslinking Monomer Trimethyl Hexamethylene Diacrylamide (3-Acrylamidopropyl)trimethylammonium chloride solution (10.0 g, 75 wt %) was mixed with 1.3-butanediol (1.5 g) and diethylene glycol methyl ether (3.5 g). To this solution was added 17.4 g of trimethyl hexamethylene diacrylamide solution from Example 5 and further mixed. IRGACURE® 2959 (2.5 g) was added and dissolved in the mixture. The formula solution was applied onto SEFAR® PET 1500 woven polyester cloth (mesh open 151 μm, open area 53%, and mesh thickness 90 μm). Excess solution was removed from the substrate by running a roller over the substrate with care being taken to exclude air bubbles from the substrate.

The solution-impregnated substrate was irradiated with UV light (wavelength 300-400 nm) for 10 min. The resulting anion exchange membrane was rinsed thoroughly in water. The anion exchange membrane had the following properties:
Membrane thickness: 0.09 mm-0.10 mm
Electrical resistance: 3.0-3.5 Ωcm2
Water content: 34.0 wt %
Ion exchange capacity: 1.7 mmol per gram of dry resin Example 22

Preparation of Cation Exchange Resin with Crosslinking Monomer Trimethyl Hexamethylene Diacrylamide A cation exchange resin was prepared using an inverse suspension polymerization strategy. The organic phase of the polymerization consisted of 100 ml of hexane containing 0.5 g of SPAN® 80 (sorbitan monooleate) (SPAN is a registered trademark of Croda International PLC, Snaith, UK). The aqueous phase of the polymerization consisted of deionized water (4.0 g), acrylamido-2-methyl-1-propanesulfonic acid (AMPS) (10.0 g), and trimethyl hexamethylene diacrylamide crosslinker solution (29.2 g) from Example 5, and 0.7 g of the free radical initiator ammonium persulfate. The aqueous phase and the organic phase were deoxygenated with nitrogen. An inverse suspension between the organic phase and the aqueous phase was formed by stirring under 300 RPM. Polymerization of the inverse suspension was then initiated by adding 0.6 ml of N,N,N',N'-tetramethylene diamine (TMEDA). The stirred polymerization was allowed to proceed for 2.5 h at room temperature. After polymerization, the mixture was filtered, the resin particles were washed with hexane (2×100 ml) and acetone (2×100 ml), and then dried at room temperature under vacuum. The cation ion exchange capacity was about 1.4 mmol per gram of dry resin. Microscopic examination revealed spherical beads with diameters in the range of 10-500 micrometers.

Example 23

Preparation of Anion Exchange Resin with Crosslikning Monomer Trimethyl Hexamethylene Diacrylamide An anion exchange resin was prepared using an inverse suspension polymerization strategy. The organic phase of the polymerization consisted of 100 ml of hexane containing 0.5 g of SPAN® 80 (sorbitan monooleate). The aqueous phase of the polymerization consisted of (3-acrylamidopropyl)trimethylammonium chloride aqueous solution (10.0 g, 75 wt %), 1,3-butanediol (2.5 g) and trimethyl hexamethylene diacrylamide crosslinker solution (21.9 g) from Example 5, and 0.55 g of the free radical initiator ammonium persulfate. The aqueous phase and the organic phase were deoxygenated with nitrogen. An inverse suspension between the organic phase and the aqueous phase was formed by stirring under 300 RPM. Polymerization of the inverse suspension was then initiated by adding 0.45 ml of N,N,N',N'-tetramethylene diamine (TMEDA). The stirred polymerization was allowed to proceed for 2.5 h at room temperature. After polymerization, the mixture was filtered, the resin particles were washed with hexane (2×100 ml) and acetone (2×100 ml), and dried at room temperature under vacuum. The anion ion exchange capacity was about 1.4 mmol per gram of dry resin. Microscopic examination revealed spherical beads with diameters in the range of about 10 to about 500 micrometers.

The invention claimed is:

1. A process for preparing a highly crosslinked ion exchange membrane comprising:
polymerizing a homogenous solution comprising:
an ionic monomer having an ionic group selected from the group consisting of sulfonic acid groups, sulfonate groups, and quaternary ammonium groups; and
an acrylamide-based crosslinking monomer having a chemical structure shown in Formula 1;

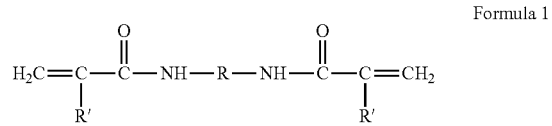

Formula 1 wherein R is selected from the group consisting of isophorone groups, methylene dicyclohexyl groups, methylene diphenyl groups, and trimethylhexamethylene groups;
wherein R' is a hydrogen atom or a methyl group; and
wherein the acrylamide-based crosslinking monomer percentage in mixed monomers of ionic monomer and the acrylamide-based crosslinking monomer is above 44 wt %.

2. The process according to claim 1, wherein the ion exchange membrane is a cation exchange membrane; and
wherein the ionic monomer is selected from the group consisting of sodium 4-vinylbenzenesulfonate, 3-sulfopropyl acrylate potassium salt, 2-acrylamido-2-methyl-1-propanesulfonic acid, and 2-acrylamido-2-methyl-1-propanesulfonic acid salts.

3. The process according to claim 1, wherein the ion exchange membrane is an anion exchange membrane; and
wherein the ionic monomer is selected from the group consisting of 3-acrylamidopropyl trimethylammonium chloride, 2-acryloyloxyethyl trimethylammonium chloride, 2-methacryloyloxyethyl trimethylammonium chloride, 3-methacryloylaminopropyl trimethylammonium chloride, and vinylbenzyl trimethylammonium chloride.

4. A process for preparing a highly crosslinked ion exchange membrane according to claim 1,
wherein the acrylamide-based crosslinking monomer is produced through a process comprising:
preparing a first solution comprising:
one of acrylic acid and methacrylic acid;
a solvent selected from the group consisting of chloroform, dichloromethane, dimethylacetamide, ethylene glycol dimethyl ether, N-methylpyrrolidone, and tetrahydrofuran; and
a catalyst selected from the group consisting of organometallic compounds, metal salts, tertiary amines, and combinations thereof;
preparing a second solution by adding into and mixing with the first solution an isocyanate compound having at least two isocyanate groups, the isocyanate compound selected from the group consisting of aliphatic isocyanates, cycloaliphatic isocyanates, oligomer isocyanates, and combinations thereof; and
mixing the second solution at a selected temperature for a period of time sufficient for formation of the acrylamide-based crosslinking monomer.

* * * * *